US00PP31225P2

(12) United States Plant Patent
Kerley et al.

(10) Patent No.: US PP31,225 P2
(45) Date of Patent: Dec. 10, 2019

(54) ***PRIMULA VULGARIS* 'KERBELCARMEN'**

(50) Latin Name: *Primula vulgaris*
Varietal Denomination: KERBELCARMEN

(71) Applicants: Priscilla Kerley, Cambridge (GB); David Kerley, Cambridge (GB); Sarah Kerley, Cambridge (GB); Timothy Kerley, Cambridge (GB)

(72) Inventors: Priscilla Kerley, Cambridge (GB); David Kerley, Cambridge (GB); Sarah Kerley, Cambridge (GB); Timothy Kerley, Cambridge (GB)

( * ) Notice: Subject to any disclaimer, the term of this patent is extended or adjusted under 35 U.S.C. 154(b) by 0 days.

(21) Appl. No.: 15/998,357

(22) Filed: Aug. 7, 2018

(30) Foreign Application Priority Data

Jul. 27, 2018 (QZ) ..... PBR 201802450

(51) Int. Cl.
*A01H 5/02* (2018.01)

(52) U.S. Cl.
USPC ..... Plt./472

(58) Field of Classification Search
USPC ..... Plt./472
See application file for complete search history.

*Primary Examiner* — Annette H Para
(74) *Attorney, Agent, or Firm* — Cassandra Bright

(57) ABSTRACT

A new and distinct *Primula vulgaris* cultivar named 'KERBELCARMEN' is disclosed, characterized by light red, large double flowers, with enlarged sepals, strong peduncles, and freely flowering. Plants have shown the ability to be propagated by tissue culture at a good rate. The new variety is a *Primula vulgaris*, suitable for outdoor landscape and container use.

2 Drawing Sheets

Figure 1:
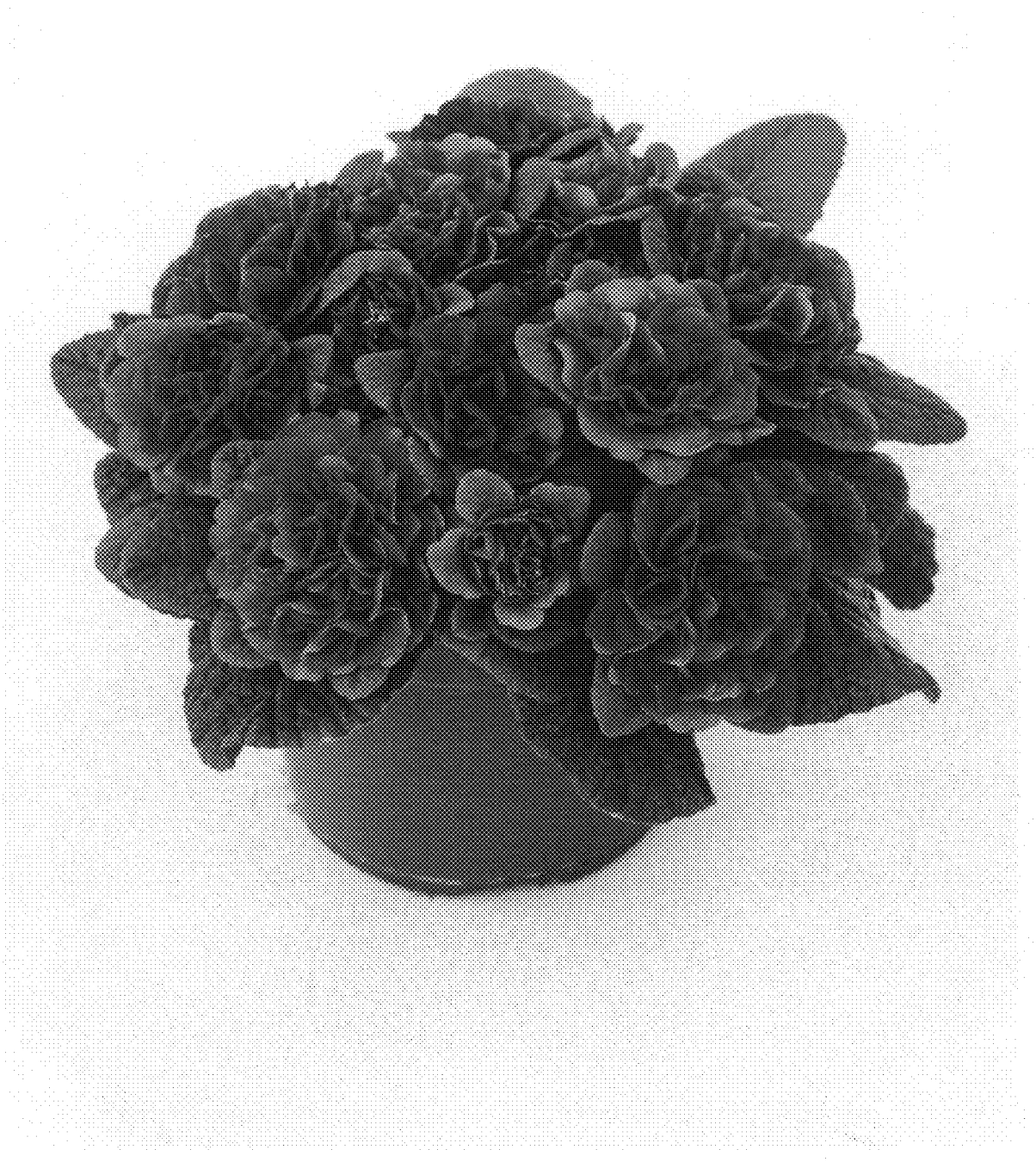

Latin name of the genus and species: *Primula vulgaris.*
Variety denomination: 'KERBELCARMEN'.

BACKGROUND OF THE INVENTION

The new cultivar is the product of a planned breeding program under the direction of the inventors, David Kerley, Priscilla Kerley, Sarah Kerley, and Timothy Kerley, all citizens of the United Kingdom. The objective of the breeding program was to produce new, compact pot-type *Primula vulgaris* cultivars with abundant double flowers for commercial ornamental purposes. The new cultivar resulted from crossing of the seed parent, the unpatented, proprietary variety *Primula vulgaris* '08-225-3', and the pollen parent, the unpatented, proprietary variety *Primula vulgaris* '08-170-1'. The selection of the new variety 'Kerbelcarmen' was made in February 2010, by the inventors at a research greenhouse located in Cambridge, UK.

Asexual reproduction of the new cultivar 'KERBELCARMEN' by division was first performed at the same research greenhouse in Cambridge, UK during September of 2010, by division and tissue culture. Both methods have shown that the unique features of this cultivar are stable and reproduced true to type in successive generations.

SUMMARY OF THE INVENTION

The cultivar 'KERBELCARMEN' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'KERBELCARMEN' These characteristics in combination distinguish 'KERBELCARMEN' as a new and distinct *Primula* cultivar:

1. Rosy red flowers (no other double *Primula vulgaris* with this color to the best of our knowledge).
2. Early flowering,
3. Enlarged sepals behind the flower.
4. Double flowers.
5. Large flowers.
6. Strong peduncles.
7. Good propagation rate in tissue culture.

PARENT COMPARISON

Plants of the new cultivar 'KERBELCARMEN' are similar to plants of the seed parent, proprietary seedling '08-225-3', in most horticultural characteristics. However, plants of the new cultivar differ in the following ways:

1. New cultivar has double flowers; seed parent is single flowered.
2. New variety is sterile; seed parent is fertile.
3. Flowers of new variety are long lasting; seed parent's flowers do not last as long.
4. New cultivar has a long flowering period; parent ceased flowering when seed had set.
5. New variety has an enlarged calyx; parent has a normal calyx.
6. New variety's flower color is carmine red; seed parent's is orange-scarlet.

Plants of the new cultivar 'KERBELCARMEN' are similar to plants of the pollen parent, proprietary seedling 08-170-1, in most horticultural characteristics. However, plants of the new cultivar differ in the following ways:

1. New cultivar has double flowers; pollen parent is single flowered.

2. New variety is sterile; seed parent is fertile.
3. Flowers of new variety are long lasting; pollen parent's flowers do not last as long.
4. New cultivar has a long flowering period; parent ceased flowering when seed had set under natural conditions.
5. New variety's flower color is carmine red; pollen parent's is red.
6. Flowering time for new variety is much earlier than that of pollen parent.

COMMERCIAL COMPARISON

Plants of the new variety can be compared to plants of the *Primula vulgaris* cultivar 'Kerbelred' (U.S. Plant Pat. No. 24,691). In side-by-side comparisons conducted in Over, Cambridge, United Kingdom, plants of the new *Primula* differed from plants of the cultivar 'Kerbelred' in the following characteristics:

1. New variety's flower is color 59A, flushed N57A; comparator's color is 53B.
2. New cultivar's flower diameter 4.4 cm; comparator's diameter is 4 cm.
3. Flowering time for new variety is about 4 weeks earlier than that of comparator, depending on climate.

Plants of the 'KERBELCARMEN' can be compared to plants of the *Primula vulgaris* cultivar 'Corporal Baxter', not patented. In side-by-side comparisons conducted in Over, Cambridge, United Kingdom, plants of the new *Primula* differed from plants of the cultivar 'Corporal Baxter' in the following characteristics:

1. Flower color of new cultivar is a carmine red; comparator is red to crimson.
2. New cultivar's flower size is large; comparator's is small to medium.
3. New variety has an enlarged calyx—jack in the green; comparator has a normal calyx.
4. New variety has a short, stiff peduncle; comparator has a medium-long, thin peduncle.

Plants of the 'KERBELCARMEN' can be compared to plants of the *Primula vulgaris* cultivar 'Captain Blood', not patented. In side-by-side comparisons conducted in Over, Cambridge, United Kingdom, plants of the new *Primula* differed from plants of the cultivar 'Corporal Baxter' in the following characteristics:

1. Flower color of new cultivar is a carmine red; comparator is deep red to crimson.
2. New cultivar's flower size is large; comparator's is small to medium.
3. New variety has an enlarged calyx—jack in the green; comparator has a normal calyx.
4. New variety has a short, stiff peduncle; comparator has a medium-long, thin peduncle.

BRIEF DESCRIPTION OF THE PHOTOGRAPHS

The accompanying photograph in FIG. 1 illustrates in full color typical plants of 'KERBELCARMEN' grown in Over, Cambridge, United Kingdom, in a glass-covered greenhouse and under commercial production practices during the spring. Plants were about four to five months old when the photographs were taken. During the production of the plants, day temperatures ranged from 5 to 15 degree C. and night temperatures ranged from 2 to 12 degree C.

Figure 2:
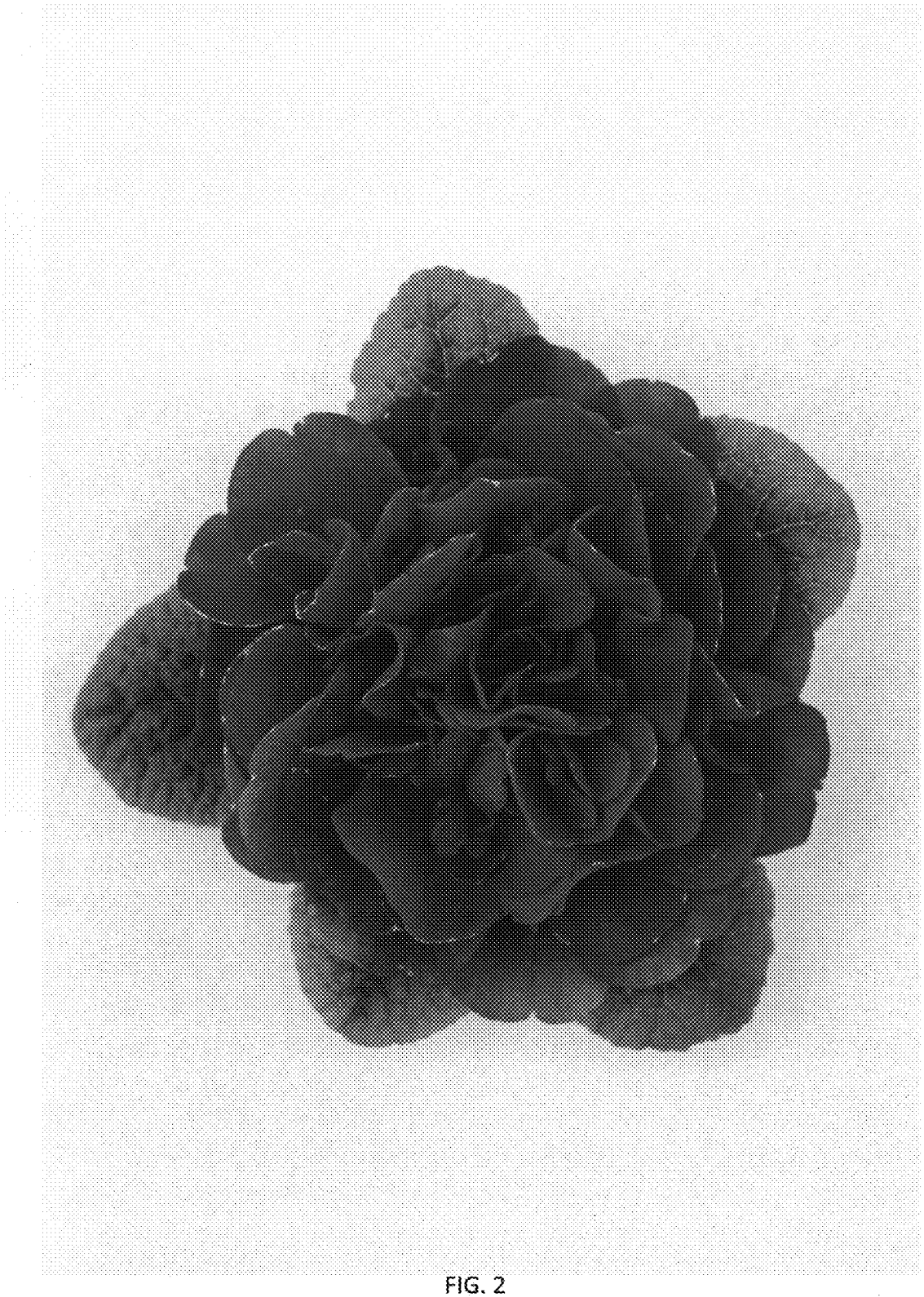

FIG. 2 illustrates a close up of a typical flower of 'KERBELCARMEN'.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Color Chart, 1995 except where general terms of ordinary dictionary significance are used. The following observations and measurements describe 'KERBELCARMEN' plants grown under commercial production practices during the spring in Cambridge, United Kingdom. During the production of the plants, day temperatures ranged from 5 to 15-degree C. and night temperatures ranged from 2 to 12-degree C. No chemical or photoperiodic treatments were given. Measurements and numerical values represent averages of typical flowering types.

Botanical classification: *Primula vulgaris* 'KERBELCARMEN'.

Age of the plant described: Approximately 4 to 5 months in an 11 cm pot.

PROPAGATION

Method: Tissue culture.

Time to initiate roots: About four weeks at 20° C.

Time to produce a rooted young plant: About six weeks at 20° C.

Root description: Fibrous, colored near RHS White 155A.

PLANT

Growth habit: Upright, compact and uniform. Inverted triangle. Vigorous.

Height: Approximately 12 to 17 cm.

Plant spread: Approximately 23 cm.

Branching characteristics: No branches, foliage emerges basally.

FOLIAGE

Leaf:

*Arrangement.*—Basal, simple.

*Average length.*—Approximately 10 cm.

*Average width.*—Approximately 3.5 to 5.5 cm.

*Shape of blade.*—Oblanceolate.

*Apex.*—Obtuse.

*Base.*—Acute.

*Margin.*—Slightly crenate, irregular. Somewhat undulate.

*Texture of top surface.*—Smooth, slightly rugose.

*Texture of bottom surface.*—Veins prominent, slightly rugose.

*Color.*—Developing foliage upper side: Near RHS 146A. Developing foliage under side: Near RHS 146B. Mature foliage upper side: Near RHS 137A. Mature foliage under side: Near RHS 147A.

*Venation.*—Type: Pinnate. Venation color upper side: Near RHS 145C and 145D. Venation color under side: Near RHS 145C.

Petiole:

*Length.*—Approximately 2.0 to 3.5 cm.

*Diameter.*—5 to 6 mm.

*Color*.—Upper Surface: Near RHS 145C-D, sometimes tinged 186D towards base of developing leaves. Lower Surface: Near RHS 145C, sometimes tinged 186D towards base, more prominent on developing leaves.

*Texture all surfaces*.—Glabrous, smooth, slightly hirsute margins.

FLOWER

Bloom period: Recurrent flowering during the Spring under United Kingdom outdoor conditions. Very free flowering.

Inflorescence: Solitary, rounded double flowers, upright and outwardly facing.

Persistent or self-cleaning: Persistent.

Fragrance: None.

Flowers per plant: 45-72 flowers and buds.

Flower bud:

*Height*.—1.4 to 1.8 cm.

*Diameter*.—0.8 to 1 cm.

*Shape*.—Ovoid.

*Color*.—RHS 144A.

Individual flower:

*Diameter*.—3.7 to 4.4 cm.

*Depth*.—2.5 to 3.3 cm.

*Petals*.—38 to 53 per flower, in several concentric whorls.

*Length* (*including tube*).—2.2 to 2.5 cm.

*Width*.—1.4 to 1.7 cm.

*Shape*.—Obcordate.

*Apex*.—Emarginate.

*Margin*.—Mostly entire.

*Texture, upper and lower surfaces*.—Glabrous, satiny.

*Color*.—Developing petals, upper surface: RHS 53A and 53B, colors present individually. Developing petals, lower surface: RHS 60B. Mature petals, upper surface: RHS, 59A flushed Red-Purple N57A, fading to near 60C as flower matures. Mature petals, Lower surface: RHS 60B.

*Sepals*.—Quantity per flower: 5 in a single whorl; fused at base; large and "frame" the flower. Length: 2.5 to 3.5 cm. Width: 1.2 to 2.2 cm. Shape: Oblong. Apex: Obtuse. Texture, upper and lower surfaces: Smooth, glabrous, slightly rugose. Color, upper surface: RHS 144A. Color, lower surface: RHS 144A-B.

Peduncle:

*Peduncle length*.—11 to 13 cm.

*Peduncle diameter*.—2 to 2.5 mm.

*Orientation*.—Erect.

*Strength*.—Strong.

*Color*.—Near RHS 145B, fading to 145D at base.

*Texture*.—Pubescent.

REPRODUCTIVE ORGANS

Development of reproductive organs has not been observed.

OTHER CHARACTERISTICS

Disease resistance: Plants of the new *Primula* have not been noted to be resistant to pathogens and pests common to *Primula*.

Temperature tolerance: Plants of the new *Primula* have been observed to have tolerated temperatures from about −5 to 28 degrees C.

Fruit/seed production: Fruit and seed production not observed, flowers are sterile.

What is claimed is:

1. A new and distinct cultivar of *Primula* plant named 'KERBELCARMEN' as herein illustrated and described.

* * * * *